(12) United States Patent
Lee et al.

(10) Patent No.: US 8,211,695 B2
(45) Date of Patent: Jul. 3, 2012

(54) ISOLATED TRANSGENIC MAMMALIAN NEURAL CELL FOR DETECTION OF A SAMPLE CONTAINING A CHEMICAL SUBSTANCE DAMAGE TO NEUROLOGICAL SYSTEM OR SELECTION OF DRUGS FOR TREATING NEURODEGENERATIVE DISORDERS

(75) Inventors: Yi-Hsuan Lee, Taipei (TW); Cheng-Yu Wang, Taipei (TW); Shu-Hui Juan, Taipei (TW); Wen-Liang Chen, Taipei (TW); Kuo-Sheng Hung, Taipei (TW); Chun-Hua Lin, Taipei (TW)

(73) Assignee: Taipei Medical University, Taipei (TW)

( * ) Notice: Subject to any disclaimer, the term of this patent is extended or adjusted under 35 U.S.C. 154(b) by 31 days.

(21) Appl. No.: 12/751,718

(22) Filed: Mar. 31, 2010

(65) Prior Publication Data

US 2011/0244470 A1  Oct. 6, 2011

(51) Int. Cl.
*C12N 5/00* (2006.01)
*C12N 5/02* (2006.01)
*C12Q 1/00* (2006.01)
*C12Q 1/68* (2006.01)

(52) U.S. Cl. ............ 435/325; 435/4; 435/6.1; 435/6.13; 435/6.16; 435/6.18

(58) Field of Classification Search .................. None
See application file for complete search history.

(56) References Cited

U.S. PATENT DOCUMENTS

| | | | |
|---|---|---|---|
| 5,378,822 A * | 1/1995 | Bradfield et al. | 536/23.5 |
| 5,854,010 A | 12/1998 | Denison et al. | |
| 6,949,354 B2 * | 9/2005 | Villa et al. | 435/29 |

OTHER PUBLICATIONS

Nebert et al. (1989) Regulation of the mammalian cytochrome P1-450 (CYP1A1) gene. Int. J. Biochem. 21(3): 243-252.*
Spires et al. (2005) Transgenic models of Alzheimer's disease: Learning from animals. NeuroRx 2: 423-437.*
Williamson et al. (2005) Aryl hydrocarbon receptor expression and activity in cerebellar granule neuroblasts: Implications for development and dioxin neurotoxicity. Toxicological Sciences 83: 340-348.*
Tracey D. Bradshaw et al., Relevance of the aryl hydrocarbon receptor (AhR) for clinical toxicology, Clinical Toxicology, 2009, 47, 632-642.
Barbara Oesch-Bartlomowicz et al., Aryl hydrocarbon receptor activation by cAMP vs. dioxin: Divergent signaling pathways, PNAS Jun. 28, 2005, vol. 102, No. 26, pp. 9218-9223.
Sandra L. Petersen et al., Distribution of mRNAs Encoding the Arylhydrocarbon Receptor, Arylhydrocarbon Receptor Nuclear Translocator, and Arylhydrocarbon Receptor Nuclear Translocator-2 in the Rat Brain and Brainstem, J. Comp. Neurol. (2000), 427(3): 428-439.
Chun-Hua Lin et al., Neuronal Activity Enhances Aryl Hydrocarbon Receptor-Mediated Gene Expression and Dioxin Neurotoxicity in Cortical Neurons, Journal of Neurochemistry, 2008, 104, pp. 1415-1429.
Hans Postlind et al., Response of Human CYP1-Luciferase Plasmids to 2,3,7,8-Tetrachlorodibenzo -p-dioxin and Polycyclic Aromatic Hydrocarbons, Toxicology and Applied Pharmacology, 1993, vol. 118, pp. 255-268.

* cited by examiner

*Primary Examiner* — Anna-Marie Falk
(74) *Attorney, Agent, or Firm* — WPAT, P.C.; Anthony King

(57) ABSTRACT

The invention is to provide an isolated transgenic mammalian neural cell, which comprises at least one heterologous vector expressing AhR/ARNT. Also provided is methods the detection of a sample containing a chemical substance damage to the nervous system and the selection of drugs for treating neurodegenerative disorders.

13 Claims, 1 Drawing Sheet

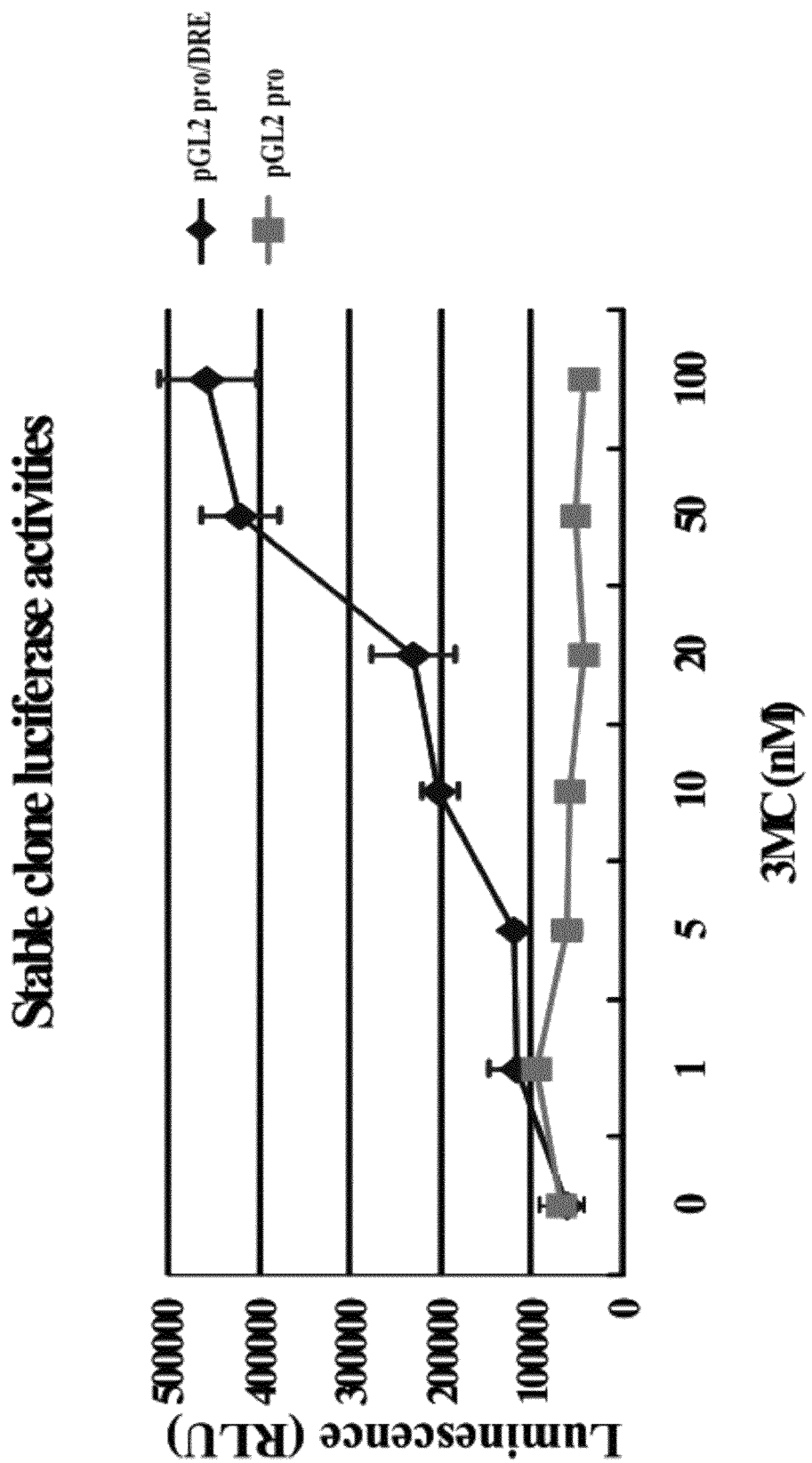

ISOLATED TRANSGENIC MAMMALIAN NEURAL CELL FOR DETECTION OF A SAMPLE CONTAINING A CHEMICAL SUBSTANCE DAMAGE TO NEUROLOGICAL SYSTEM OR SELECTION OF DRUGS FOR TREATING NEURODEGENERATIVE DISORDERS

FIELD OF THE INVENTION

The present invention relates to a cell for measuring whether a sample containing a chemical substance damage to the nervous system.

BACKGROUND OF THE INVENTION

The aryl hydrocarbon receptor (AhR) is a ligand-activated transcription factor that mediates a number of biological responses to planar aromatic hydrocarbons (PAHs). Chemicals which interact with the AhR include a variety of environmental contaminants, such as dioxins, PCBs, PAHs and benzo(a)pyrene, as well as natural products, such as flavones and carbazoles.

One of the most potent agonists of the AhR is dioxin. The term dioxin, as commonly used by the news media, is shorthand for 2,3,7,8-tetrachlorodibenzo-p-dioxin ("TCDD"). TCDD is only one member (i.e. congener) of the polychlorinated dibenzo-p-dioxin family, of which there are 75 possible congeners whose structures vary according to the number and location of the chlorine atoms. A great number of isomers that differ in the chlorine substitution patterns exist for these three types of skeletal structures. Dioxins or dioxin-like compounds are environmental pollutants that have raised public concern because of their toxicity and their ability to remain in the environment for a long time. It has become clear that dioxins with their various toxic properties are contained in chemicals such as herbicides and insecticides, exhaust gases and fly ashes from garbage incineration facilities, waste water from papermills, etc. Dioxin induces a number of receptor-mediated toxic responses, including a severe wasting syndrome, epidermal hyperplasia and metaplasia, tumor promotion and thymic involution.

AhR gene was highly conserved in amphibian, fish, and mammalian during evolution. Specific environmental and endogenous compounds were found to bind on AhR and this complex subsequently binds to DRE sequence to activate AhR downstream gene expressions. The AhR resides primarily in the cytosol, where it is associated with its molecular chaperone, Hsp90. Upon binding to an agonist, the AhR dissociates from Hsp90, translocates to the nucleus and dimerizes with a structurally related protein, aryl hydrocarbon nuclear translocator (ARNT). This complex interacts with enhancer elements upstream of target promoters and up-regulates the transcription of a variety of xenobiotic metabolizing enzymes (e.g., the cytochrome P450 encoded by CYP1A1). The AhR and ARNT are both members of the basic helix-loop-helix-PAS superfamily. The helix-loop-helix domain serves as a dimerization surface for AhR and ARNT and also positions the basic alpha-helix within the major groove of B-DNA to enable specific interactions with target enhancer elements. The PAS domain functions as a dimerization surface, harbors a repressor region, and also contains regions required for binding agonist and forming interactions with Hsp90. The AhR is essential for the toxicity of dioxins and related chemicals. The AhR mediates the exquisite sensitivity of animals to dioxins, where as little as 2 ng/kg/day can yield striking adverse effects (Tracey D. Bradshaw and David R. Bell, Clinical Toxicology, 2009, 47, 632-642). After binding of dioxin to the AhR, the activated AhR translocates rapidly from the cytosol to the nucleus and forms a heterodimer with ARNT, causing cellular responses that lead to toxicity, carcinogenesis and teratogenesis (Barabra Oesch-Bartlomowicz et al. PNAS Jun. 28, 2005, vol. 102, no. 26, pp. 9218-9223). Neurotoxicity of endocrine disruptors has been recently suspected to be a cause of neurological disorders. The endocrine disruptors exhibit various toxicity such as reproduction toxicity, immunotoxicity and neurotoxicity, and a part of toxicity is known to be expressed through AhR mediated pathway. The aryl hydrocarbon receptor is conjectured to be related to neurotoxicity since expression of the aryl hydrocarbon receptor has been detected in brain tissue (Petersen, S. L. et al., J. Comp. Neurol. (2000), 427(3): 428-439). Correlation of expression of neurological functions and developmental formation with gene expression by the aryl hydrocarbon receptor has been also suggested. Chun-Hua Lin et al. suggest that neuronal activity may facilitate AhR-mediated calcium signaling, which in turn enhances AhR-mediated gene regulation and mediated maturation-dependent dioxin neurotoxicity (Journal of Neurochemistry, 2008, 104, pp. 1415-1429).

Environmental contaminants such as dioxin are detected not only in environmental samples from the air, soils, waters and sediments of rivers, harbors and ports around big cities, etc. but also in biological samples such as foods, blood, urine and mothers' milk. Since such a widespread contamination of the environment has been a big social problem, there is a pressing need to detect dioxin exposure in the environment. Dioxin-like compounds often occur as poorly defined mixtures of these compounds in a larger matrix of other materials that make their analysis and quantitation difficult. A number of reports disclose bioassays for detection environmental contaminants such as dioxin-like compounds. Postlind et al. describe a bioassay made by binding the 5'-flanking region of human CYP1A1 into a luciferase vector, and the resultant is transfected into human hepatoma cells (Response of Human CYP1-Luciferase Plasmids to 2,3,7,8-Tetrachlorodibenzo-p-dioxin and Polycyclic Aromatic Hydrocarbons, Vol. 118, Toxicology and Applied Pharmacology, pp. 255-268 (1993)). U.S. Pat. No. 5,854,010 provides a recombinant cell line, the mouse H1L1.1 cell line, that is made by using genetic engineering techniques for inserting dioxin responsive elements upstream of a luciferase reporter gene, and then, transfecting the resultant recombinant expression plasmid, identified as pGudLuc1.1, into mouse hepatoma cells. The mouse H1L1.1 cell line is useful in a method for the quantitative analysis of polyaromatic hydrocarbons such as dioxin in samples.

The above-mentioned references use hepatoma cells as platform to detect dioxin. However, they cannot be used to evaluate the damage of dioxin to neuron cells. Therefore, the neuronal cell platform is more appropriate to screen ligands activating AhR pathway and to evaluate its impacts on neuronal tissues than that constructed in hepatocytes. There is a need to develop a neuronal cell platform in the detection of environmental pollutants and selection of drugs of treating neurological disorders.

SUMMARY OF THE INVENTION

One object of the invention is to provide an isolated transgenic mammalian neural cell, which comprises at least one heterologous vector expressing AhR/ARNT wherein the vector comprises a reporter gene operably linked to at least one dioxin responsive element (DRE), wherein the reporter gene expresses a detectable gene product as a result of an AhR ligand binding to the AhR/ARNT.

Another object of the invention is to provide a method for the detection of a sample containing a chemical substance damage to the nervous system, which comprises (i) culturing the isolated transgenic mammalian neural cell of the invention with the chemical substance, (ii) measuring the expression amount of the reporter protein encoded by the reported gene in the cell, and (iii) determining whether the sample contains a chemical substance damage to the nervous system when the value of expression amount of the reporter protein as measured in step (ii) is larger than a value of expression amount of said reporter protein as measured in a cell cultured in the absence of said chemical substance.

A further object of the invention is to provide a method for the selection of drugs for treating neurodegenerative disorders, which comprises (i) culturing the isolated transgenic mammalian neural cell of the invention with a drug candidate and an AhR agonist, (ii) measuring the expression amount of the reporter protein encoded by the reported gene in the cell, and (iii) determining whether the drug candidate is able to treat neurological disorders when the value of expression amount of the reporter protein as measured in step (ii) is smaller than a value of expression amount of said reporter protein as measured in a cell cultured only with an AhR agonist.

BRIEF DESCRIPTION OF THE DRAWING

FIG. 1 shows relative luciferase activity in AhR ligand activated C6 DRE stable clone.

DETAILED DESCRIPTION OF THE INVENTION

The invention develops a neuronal cell platform that is more appropriate to screen ligands activating AhR pathway and to evaluate its impacts on neuronal tissues than that constructed in other tissue cells (particularly, hepatocytes) because AhR ligands/AhR signaling associated tumor progression and neuron damages are tissue specific.

1. Definitions

The singular forms "a," "and," and "the" include plural referents unless the context clearly dictates otherwise. Thus, for example, reference to "a cell" includes a plurality of such cells.

The term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. An isolated nucleic acid molecule inserted into a vector is also sometimes referred to herein as a "recombinant" nucleic acid molecule.

The term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

The term "transgenic" is meant any cell which includes a DNA sequence which is inserted by artifice into a cell and becomes part of the genome of the organism which develops from that cell.

The term "transformation" is meant any method for introducing foreign molecules into a cell.

The term "transformed cell" is meant a cell into which (or into an ancestor of which) has been introduced, by means of recombinant DNA techniques, a DNA molecule encoding (as used herein) a polypeptide.

The term "promoter region" refers to the transcriptional regulatory regions of a gene, which may be found at the 5' or 3' side of the coding region, or within the coding region, or within introns.

The term "selectable marker gene" refers to a gene encoding a product that, when expressed, confers a selectable phenotype such as antibiotic resistance on a transformed cell.

As a "reporter gene" which is an indicator of transcription activity, a gene which expression amount can be measured based on the enzyme activity and the like of the transcription product thereof (reporter protein) is preferable because the measurement of the expression amount of the gene is easy, with examples thereof including genes coding enzyme proteins such as fire fly luciferase, Renilla luciferase, beta-galactosidase, chloramphenicolacetyltransferase, alkaliphosphatase and the like. DNA of such a reporter gene may be obtained, for example, by using a restriction enzyme to digest a DNA of commercially available plasmids containing such reporter genes and isolating the intended DNA, as well as by other like procedures.

The term "detectably-labeled" is meant any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as 32P or 35S), and nonradioactive labeling (e.g., chemiluminescent labeling or fluorescein labeling).

2. Isolated Transgenic Mammalian Neural Cells of the Invention

In one aspect, the invention provides an isolated transgenic mammalian neural cell, which comprises at least one heterologous vector expressing AHR/ARNT wherein the vector comprises a reporter gene operably linked to at least one dioxin responsive element (DRE), wherein the reporter gene expresses a detectable gene product as a result of an AHR ligand binding to the AhR/ARNT.

According to the invention, any mammalian neural cell suitable to transformed with DRE construct can be used in the invention. The mammalian neural cell is from mammal, preferably, human, rat, mouse, rabbit, pig or monkey.

In one embodiment of the invention, the vector comprises at least one dioxin responsive element (DRE) operably linked to a reporter gene. Preferably, the vector comprises at least two or three repeats of DRE. More preferably, at least three repeats of DRE. DRE is the sequence recognized for binding by the AhR/ARNT heterodimer. It is particularly preferred to utilize the dioxin responsive element or portions thereof to form the binding substance. The DNA sequences for the dioxin responsive element of cells in various species has been the subject of extensive investigation. Dioxin responsive element nucleotide sequences are known in the art and are disclosed in D. W. Nebert, et. al., "Minireview—Regulation of the Mammalian Cytochrome P1-450(CYPIAI) Gene", Int. J. Biochem, vol. 21, no. 3, pp. 243-52 (1989), which is hereby incorporated by reference. According to the invention, the preferred DRE sequence is selected from the group consisting of:

```
(SEQ ID NO: 1, contains 3 repeats of DRE on the
rat CYP1A1 gene promoter)
ATAGGTACCGGCTCTTCTCACGCAACTCGGCTCTTCTCACGCAACTCG
GCTCTTCTCACGCAACTCGCTAGCATA;

(SEQ ID NO: 2, contains 3 repeats of DRE on the
human NR2A gene promoter
ACAAGGGCACGCACACGGCCACAAGGGCACGCACACGGCCACAAGGGC
ACGCACACGGCC;
and (SEQ ID NO: 3, contains 3 repeats of DRE on the
rat NR2A gene promoter)
GCGGGTGTGTGCGTGTCGGCGCGGGTGTGTGCGTGTCGGCGCGGGTGT
GTGCGTGTCGGC
```

In one embodiment of the invention, the reporter gene preferably encodes an enzyme which catalyses a reaction which produces a detectable signal, preferably a visually detectable signal, such as a colored product. Many examples are known, including beta-galactosidase and luciferase. Beta-galactosidase activity may be assayed by production of blue color on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labeled directly or indirectly using any standard technique. The reporter gene is preferably selected from the group consisting of fire fly luciferase gene, Renilla luciferase gene, fluorescence protein gene such as red or green fluorescent protein gene, gus gene, beta-galactosidase gene, chloramphenicolacetyltransferase gene and alkaliphosphatase gene.

Those skilled in the art are well aware of a multitude of possible reporter genes and assay techniques which may be used to determine gene activity. Any suitable reporter/assay may be used and it should be appreciated that no particular choice is essential to or a limitation of the present invention.

A DNA containing a reporter gene may be prepared by inserting the DNA of the above-mentioned reporter gene downstream from a promoter of commercially available plasmids containing the promoter.

The cell of the invention may be prepared by integrating the DNA containing the ligand-responsive reporter gene and the DNA containing the reporter gene into vectors such as plasmids and the like, respectively, and introducing the vectors into the cell, by selecting cells in which these reporter genes are securely maintained therein. Specifically, when the transcription control factor is an allylhydrocarbon receptor, it is preferable to prepare a plasmid integrated with a fire fly luciferase (ligand-responsive transcription control factor) connected downstream from a nucleotide sequence containing a dioxin-responsive sequence derived from the 5' upstream region of cytochrome P4501A1 gene and downstream from a nucleotide sequence necessary for initiation of transcription derived from the 5' upstream region of a glutathione S-transferase Ya subunit gene, or a plasmid integrated with a Renilla luciferase gene connected downstream from a tk promoter. These plasmids are introduced into a cell endogenously expressing aryl hydrocarbon receptor. In such cases, an expression plasmid of a selective marker gene such as a chemical-resistant gene and the like may also be introduced simultaneously, to provide easy selection of the cells into which these reporter genes have been introduced. Examples of the chemical-resistant gene which may be used as described above include a neomycin-resistant gene (aminoglycoside phosphotransferase), blasticidin S-resistant gene, hygromycin-resistant gene and the like.

To introduce the DNA of a plasmid integrated with the above-mentioned reporter gene into, for example, cells derived from mammalian animals, first, for example, the cells are placed in a culturing vessel and cultured for a period of time at appropriate temperature under suitable conditions. Into the thus cultured cells, plasmid DNA integrated with reporter gene is introduced. As the method for introducing DNA into a cell, a conventional lipofection method, DEAE-dextran method, calcium phosphate method, electroporation method, virus infection method, PEG-mediated transformation method, Deliver X peptide method, nano-particle-mediated endocytosis method, gene gun, microinjection, and the like are listed. After introduction of a plasmid DNA into the cell, the medium is substituted with a serum-containing medium, and the culturing is continued for an appropriate time. Next, the cell is removed from the culturing vessel by trypsinization or the like according to a conventional method and transferred a new culturing vessel. Directly after being transferred, or after culturing for 1 to 2 days, the medium is substituted with a medium having conditions corresponding to a selective marker gene introduced into the cell, and the culturing is continued in the medium having conditions corresponding to a selective marker gene until non-transformed cells disappear and a colony derived from the transformed cell becomes an appropriate size. By conducting such procedures, the cell securely maintaining the reporter gene therein can be obtained so that the stable transformed cell can be recovered. To confirm that the introduced reporter gene is securely maintained in the cell, it may be advantageous to prepare the DNA of this cell according to a conventional genetic engineering procedure, and to detect the presence of this reporter gene by utilizing a method such as PCR, southern hybridization method and the like using as a primer, a probe, a DNA fragment having a partial nucleotide sequence of the introduced reporter gene or the like.

Typical expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Some vectors contain selectable markers such as neomycin resistance that permit isolation of cells by growing them under selective conditions. Cell lines may also be produced which have integrated the vector into the genomic DNA and in this manner the gene product is produced on expression vectors contain promoters that direct the synthesis of large amounts of mRNA corresponding to the gene. They may also include sequences allowing for their autonomous replication within the host organism, sequences that encode genetic traits that allow cells containing the vectors to be selected, and sequences that increase the efficiency with which the mRNA is translated. Some vectors contain selectable markers such as neomycin resistance that permit isolation of cells by growing them under selective conditions. Stable long-term vectors may be maintained as freely replicating entities by using regulatory elements of viruses. Cell lines may also be produced which have integrated the vector into the genomic DNA using techniques known in the art.

Regarding the expression amounts of a reporter gene, by subtracting the expression amount in a control district from the expression amount in a ligand addition district, the increase in the expression amount of the reporter gene by contact with the ligand is determined. Then, cells may be selected in which the increase in the expression amount of a reporter gene by contact with the ligand is at least 2-fold, preferably 10-fold or more of the expression amount in a control district.

3. Methods for Detecting whether a Sample Containing Chemical Substance Damage to Neurological System and Selection of Drugs for Treating Neurodegenerative Disorders In another aspect, the invention provides a method for the detection of a sample containing a chemical substance damage to neurological system, which comprises (i) culturing the isolated transgenic mammalian neural cell of the invention with the chemical substance, (ii) measuring the expression amount of the reporter protein encoded by the reported gene in the cell, and (iii) determining whether the sample contains a chemical substance damage to the nervous system when the value of expression amount of the reporter protein as measured in step (ii) is larger than a value of expression amount of said reporter protein as measured in a cell cultured in the absence of said chemical substance. According to the invention, the cell is allowed to contact with a chemical substance in a similar manner as described above, and the expression amount of the reporter gene is quantified. When the expression amount of a reporter gene of the cell increases by contact of the chemical substance, it is suggested that this chemical substance shows damage to neurological system. According to the invention, the chemical substance is preferably a AhR agonist. For example, the AhR agonist is PCDDs, PCDFs, and dioxin-like PCBs, dioxin, halogenated naphthalenes, halogenated diphenyl ethers, halogenated azo- and azoxybenzenes or polycyclic aromatic hydrocarbons (PAHs).

In further another aspect, the invention provides a method for the selection of drugs for treating neurodegenerative disorders, which comprises (i) culturing the isolated transgenic mammalian neural cell of the invention with a drug candidate in combination with an AhR agonist, (ii) measuring the expression amount of the reporter protein encoded by the reported gene in the cell, and (iii) determining whether the drug candidate is able to treat neurological disorders when the value of expression amount of the reporter protein as measured in step (ii) is smaller than a value of expression amount of said reporter protein as measured in a cell cultured only treated with AhR agonist.

According to the invention, for example, the AhR agonist is PCDDs, PCDFs, dioxin-like PCBs, dioxin, halogenated naphthalenes, halogenated diphenyl ethers, halogenated azo- and azoxybenzenes or polycyclic aromatic hydrocarbons (PAHs).

N-methyl-D-aspartic acid (NMDA) receptors are ligand-gated calcium channels that play pivotal roles in synaptic development and plasticity, activity-dependent neuronal survival and excitotoxic cell death in the central nervous system. NMDA excitotoxicity is the major pathophysiology of various neurodegenerative disorders, such as Alzheimer's disease, Parkinson's disease, schizophrenia and traumatic brain injury (Proc Natl Acad Sci USA, 2004, 101, 5117-2122). It is reported in Journal of Neurochemistry, 2008, 104, pp. 1415-1429 that knockdown of AhR gene expression attenuates NMDA-induced excitotoxicity accompanied by reduction of NMDA receptor expression and activity. Therefore, the isolated transgenic mammalian neural cell of the invention can be used to select a drug candidate for treating neurodegenerative disorders (preferably, Alzheimer's disease, Parkinson's disease, schizophremia and traumatic brain injury) by evaluating AhR gene expression.

The isolated transgenic mammalian neural cell of the invention is a neuronal cell platform appropriate to screen ligands activating AhR pathway and to evaluate its impacts on neuronal tissues. The neural cell of the invention also can be used to screen drug candidates for treating neurodegenerative disorders.

EXAMPLE

The plasmid pGL-2 pro/DRE was constructed by inserting a synthesized DNA fragment containing three rat dioxin responsive element (DRE, ATAGGTACCGGCTCTTCT-CACGCAACTCGGCTCTTCTCACG-CAACTCGGCTCTTCTCA CGCAACTCGCTAGCATA; SEQ ID NO:1) between the KpnI and NheI sites of pGL2-promoter (pGL2 pro). To generate pGL-2 pro/DRE stable clones, plasmids pGL-2 pro/DRE and pCMV-Tag 2B were co-transfected into C6 glioma cells by Lipofectamine™ 2000. Meanwhile, plasmid pGL-2 pro and pCMV-Tag 2B were followed the same conditions to generate pGL-2 control cell line. These transfected cells were selected by Geneticin® (G418, 500 μg/ml) for 18 days. The stable clones of C6 cells were obtained and maintained in DMEM with 10% FBS and G418. To examine the stably insertion of pGL-2 pro/DRE or pGL-2 pro, the G418 resistant cells were harvested to extracted genomic DNA for polymerase chain reaction (PCR). The inserted DNA was confirmed to amplify 392 bps for pGL-2 pro/DRE stable insertion or 324 bps for pGL-2 pro (pGL-2) stable insertion, respectively. Finally, the metabolic degradable AhR agonist, 3-methylcholanthere (3MC), was used to examine the luciferase activity of pGL-2 pro/DRE C6 stable clones.

The metabolic degradable AhR agonist, 3-methylcholanthere (3MC), was used to examine the DRE driven luciferase activity of C6 DRE stable clone and pGL2 control cell line. As shown in FIG. 1, 3MC was found to increase luminescence in a dose response only in DRE stable clone, and this result indicates that C6 DRE stable clone was able to detect AhR ligand with remarkable sensitivity. The result also reveals that C6 DRE stable clone cells were fitting for detecting AhR ligand among environmental pollutants; screening drug candidates and clinical application in neuronal and psychiatric diseases diagnostics such as, depression and Alzheimer's disease.

What is claimed is:

1. An isolated transgenic mammalian neural cell, which comprises at least one heterologous vector comprising a reporter gene operably linked to at least three repeats of a dioxin responsive element (DRE) and operably linked to a promoter, wherein the reporter gene expresses a detectable gene product and wherein the three repeats of a DRE have the sequence of SEQ ID NO: 1, SEQ ID NO:2 or SEQ ID NO:3.

2. The isolated transgenic mammalian neural cell of claim 1, wherein the reporter gene is selected from the group consisting of fire fly luciferase gene, Renilla luciferase gene, fluorescence protein gene, gus gene, beta-galactosidase gene, chloramphenicolacetyltransferase gene and alkaline phosphatase gene.

3. The isolated transgenic mammalian neural cell of claim 1, wherein the reporter gene is firefly luciferase gene or Renilla luciferase gene.

4. The isolated transgenic mammalian neural cell of claim 1, wherein the reporter gene is firefly luciferase gene.

5. A method for the detection of a chemical substance capable of damaging the nervous system, which comprises (i) culturing the isolated transgenic mammalian neural cell of claim 1 with the chemical substance, (ii) measuring the expression amount of the reporter protein encoded by the reporter gene in the cell, and (iii) determining that the chemical substance is capable of damaging the nervous system when the value of the expression amount of the reporter protein as measured in step (ii) is larger than a value of expression amount of said reporter protein as measured in a cell cultured in the absence of said chemical substance.

6. The method of claim 5, wherein the chemical substance is an AhR agonist.

7. The method of claim 5, wherein the chemical substance is PCDDs, PCDFs, dioxin-like PCBs, dioxin, halogenated naphthalenes, halogenated diphenyl ethers, halogenated azo- and azoxybenzenes or polycyclic aromatic hydrocarbons (PAHs).

8. The method of claim 5, wherein the chemical substance is dioxin.

9. A method for the selection of a drug candidate for treating a neurodegenerative disorder, which comprises (i) culturing the isolated transgenic mammalian neural cell of claim 1 with a drug candidate in combination with an AhR agonist, (ii) measuring the expression amount of the reporter protein encoded by the reporter gene in the cell, and (iii) determining that the drug candidate is able to treat a neurodegenerative disorder when the value of the expression amount of the reporter protein as measured in step (ii) is smaller than the value of the expression amount of said reporter protein as measured in a cell cultured with the AhR agonist in the absence of the drug candidate.

10. The method of claim 9, wherein the AhR agonist is PCDDs, PCDFs, dioxin-like PCBs, dioxin, halogenated naphthalenes, halogenated diphenyl ethers, halogenated azo- and azoxybenzenes or polycyclic aromatic hydrocarbons (PAHs).

11. The method of claim 5, wherein the neurodegenerative disorder is Parkinson's disease, schizophrenia or traumatic brain injury.

12. The isolated transgenic mammalian neural cell of claim 1, wherein the mammal is human, rat, mouse, rabbit, pig or monkey.

13. The isolated transgenic mammalian neural cell of claim 2, wherein the fluorescence protein gene is red, green or yellow fluorescence protein gene.

* * * * *

SEQUENCE LISTING

<160> NUMBER OF SEQ ID NOS: 3

<210> SEQ ID NO 1
<211> LENGTH: 75

```
<212> TYPE: DNA
<213> ORGANISM: Artificial Sequence
<220> FEATURE:
<223> OTHER INFORMATION: Synthetic sequence

<400> SEQUENCE: 1
ataggtaccg gctcttctca cgcaactcgg ctcttctcac gcaactcggc tcttctcacg      60
caactcgcta gcata                                                      75

<210> SEQ ID NO 2
<211> LENGTH: 60
<212> TYPE: DNA
<213> ORGANISM: Artificial Sequence
<220> FEATURE:
<223> OTHER INFORMATION: Synthetic sequence

<400> SEQUENCE: 2
acaagggcac gcacacggcc acaagggcac gcacacggcc acaagggcac gcacacggcc      60

<210> SEQ ID NO 3
<211> LENGTH: 60
<212> TYPE: DNA
<213> ORGANISM: Artificial Sequence
<220> FEATURE:
<223> OTHER INFORMATION: Synthetic sequence

<400> SEQUENCE: 3
gcgggtgtgt gcgtgtcggc gcgggtgtgt gcgtgtcggc gcgggtgtgt gcgtgtcggc      60
```